United States Patent [19]
Thornton

[11] Patent Number: 5,112,343
[45] Date of Patent: May 12, 1992

[54] ENDOSCOPIC CLIP APPLIERS

[75] Inventor: Curtis W. Thornton, Cary, N.C.

[73] Assignee: Edward Weck Incorporated, Princeton, N.J.

[21] Appl. No.: 681,212

[22] Filed: Apr. 5, 1991

[51] Int. Cl.[5] ............................................. A61B 17/00
[52] U.S. Cl. ..................................... 606/143; 606/142
[58] Field of Search ................. 606/142, 143; 227/901

[56] References Cited

U.S. PATENT DOCUMENTS

| | | | |
|---|---|---|---|
| 4,448,193 | 5/1984 | Ivanov | 606/143 |
| 4,509,513 | 4/1985 | McGarry et al. | 606/143 |
| 4,522,207 | 6/1985 | Klieman et al. | 606/143 |
| 4,532,925 | 8/1985 | Blake, III | 606/143 |
| 4,576,166 | 3/1986 | Montgomery et al. | 606/143 |
| 4,598,711 | 7/1986 | Deniega | 606/143 |
| 4,611,595 | 9/1986 | Klieman et al. | 606/143 |
| 4,616,650 | 10/1986 | Green et al. | 606/143 |
| 4,624,254 | 11/1986 | McGarry et al. | 606/143 |
| 4,662,373 | 5/1987 | Montgomery et al. | 606/143 |
| 4,662,374 | 5/1987 | Blake, III | 606/143 |
| 4,674,504 | 6/1987 | Klieman et al. | 606/143 |
| 4,712,549 | 12/1987 | Peters et al. | 606/143 |

*Primary Examiner*—Stephen C. Pellegrino
*Assistant Examiner*—Gary Jackson
*Attorney, Agent, or Firm*—Gene Warzecha

[57] ABSTRACT

A hemostatic clip applier is disclosed showing improvements which enable the user to selectively trigger the feeding of a clip to the jaws of the applier when desired. A cantilevered trigger button is integrally formed with the housing of the applier so as to be depressible by the user. The trigger button is provided with an internal cam surface which cooperates with a pawl and ratchet mechanism to release the pawl at a selected point in the cycle of operation of the applier and thereby feed a clip to the applier jaws.

6 Claims, 9 Drawing Sheets

ENDOSCOPIC CLIP APPLIERS

BACKGROUND OF THE INVENTION

1. Field of the Invention

The invention relates generally to endoscopic type medical devices incorporating a body or housing to which is attached some actuating mechanism at one, proximal end and a working mechanism at the other, distal end, the working mechanism being suitable for either applying surgical ligating clips, use as forceps, etc. More particularly, the invention relates to an improvement in endoscopic type instruments which enables the instrument to operate in its normal mode only after a trigger mechanism is selectively activated.

2. Description of the Prior Art

Surgical ligating or hemostatic clips ar used to ligate blood vessels, ducts or other tissue during surgery. The terms "ligating" and "hemostatic" are used interchangeably herein. The clips generally have two parallel legs which are crimped in place about the tissue to be ligated and are applied with a clip applying instrument used to crimp the clip legs together. When first introduced many years ago, each clip to be applied had to be picked up individually by the jaws of a so-called "manual" clip applying, forceps-type instrument, often from a separate clip cartridge or dispenser prior to each use. While manual appliers are still used, subsequent instruments produced were "automatic" clip appliers (some of them disposable) and incorporated a clip dispenser as part of the clip applying instrument. Since different surgical procedures require the use of varying numbers of ligating clips, the automatic appliers come pre-loaded with different numbers of clips and in varying sizes. See, for example, U.S. Pat. No. 4,712,549 (Peters et al.), assigned to the assignee of this invention.

In addition to the clip dispenser, the automatic instruments generally include a pair of jaws for receiving, holding and crimping a single clip at a time and a feeding means for feeding a clip from the dispenser to the jaws. The jaws and feeder are activated in proper sequence by an activating means usually including a pair of handles coupled mechanically to the feeder and jaws.

It has been noted by those skilled in the art that the use of hemostatic clip appliers in endoscopic surgical procedures requires some additional precautions over and above those available in appliers described above which are primarily intended for use in open surgical procedures. For example, in endoscopic surgical procedures it is desirable for the surgeon to select the point in time when a ligating clip is to be fed between the jaws of the clip applier. This prevents the possibility that a clip would be waiting between the jaws of a clip applier (as in some conventional clip appliers used in open surgical procedures) and thereby run the risk of becoming dislodged and falling uncontrollably into the body. Retrieving such accidentally dislodged clips in open surgical procedures is relatively easy, if necessary, although much more difficult in endoscopic procedures.

The assignee of the present invention has a pending U.S. patent application Ser. No. 375,174, filed Jul. 3, 1989, now a FWC of U.S. Pat. No. 07/684,139, which discloses an automatic hemostatic clip applier which has a unique operating mechanism employing a "ratchet" yoke mechanism interposed between the activating handles of the applier and the clip feeding and jaw closing structures in order to prevent undesired feeding of the clip to the jaws during a portion of the operating cycle of the applier. This instrument automatically enables the feeding of a clip at a certain part of the cycle of operation of the applier. The present invention is an improvement on this aforementioned device in that it gives the user control over the feeding of the clip and, consequently, produces an applier suitable for use in endoscopic as well as open procedures. The present application incorporates the prior application by reference in its entirety.

It is an object of this invention to produce a clip applier which enables the surgeon to select the point in time at which a ligating or hemostatic clip is to be placed in proper position for use.

It is a further object of this invention to produce a ligating or hemostatic clip applier suitable for use in endoscopic surgical procedures

SUMMARY OF THE INVENTION

These and other objects of the invention ar achieved by the preferred embodiment which is an improvement in a ligating clip applier which enables the user to select the point in time when a clip is to be placed in position for crimping. The invention is embodied in an instrument for applying ligating clips, the instrument comprising a housing, a first activating mechanism for feeding the clips successively to a position in which they may be crimped and a second activating mechanism for crimping a clip at said position. The improvement comprises a trigger means for selectively enabling the operation of the first activating mechanism, the trigger means comprising pawl means operatively secured to the first activating mechanism and adapted to slide along a predetermined track. A pawl post is attached to the pawl means and is laterally deflectable from a normal, unbiased position to a biased position as the pawl means slides in the track. A ramp means is fixedly situated relative to the track and is adapted to have the pawl post slidably move along the ramp means as the pawl means slides proximally. A stop means is provided to prevent the pawl post from moving distally beyond a predetermined point and a disengagement means is provided to disengage the pawl post from the stop means.

DESCRIPTION OF THE PREFERRED EMBODIMENT

Figure 1:
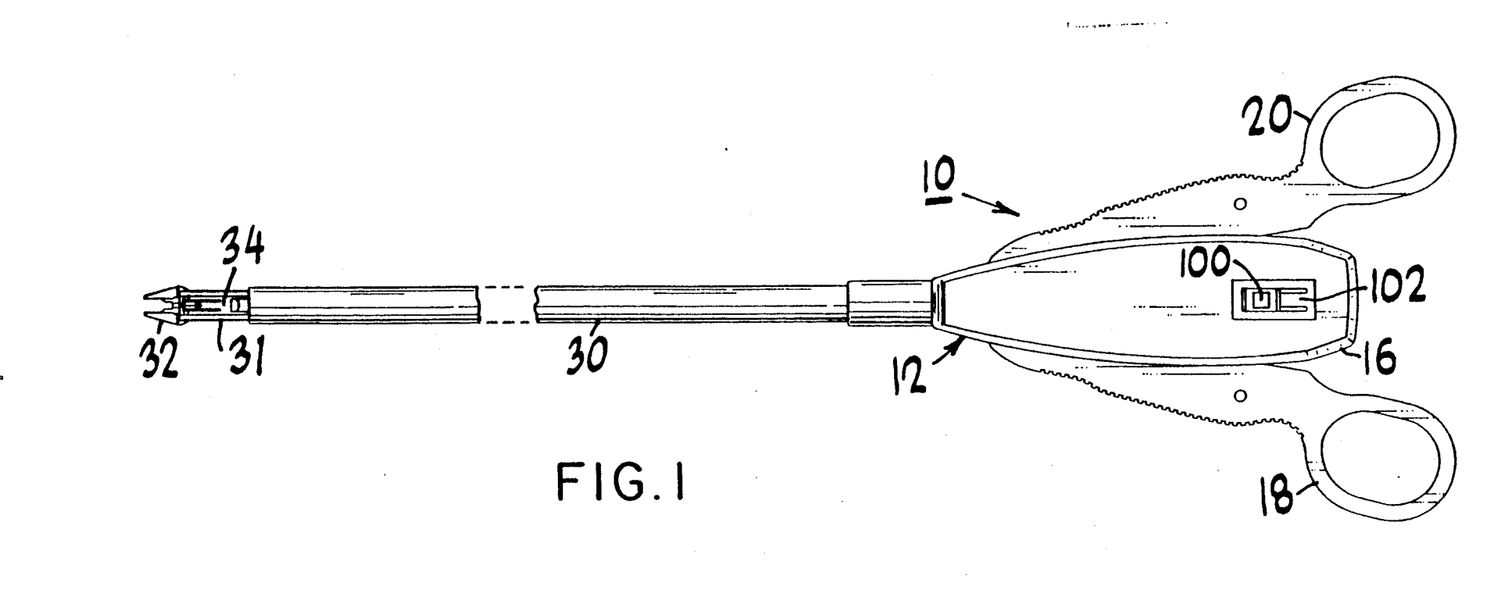
FIG. 1 is a plan view of an endoscopic hemostatic clip applier constructed in accordance with the principles of this invention.
Figure 2:
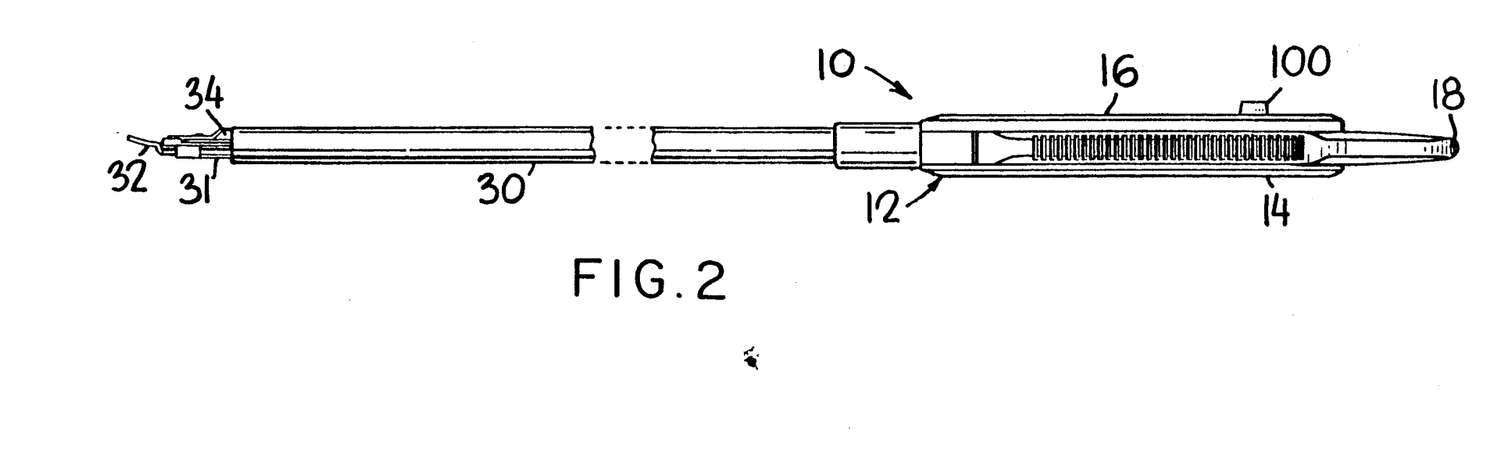
FIG. 2 is a side elevational view of FIG. 1.
Figure 3:
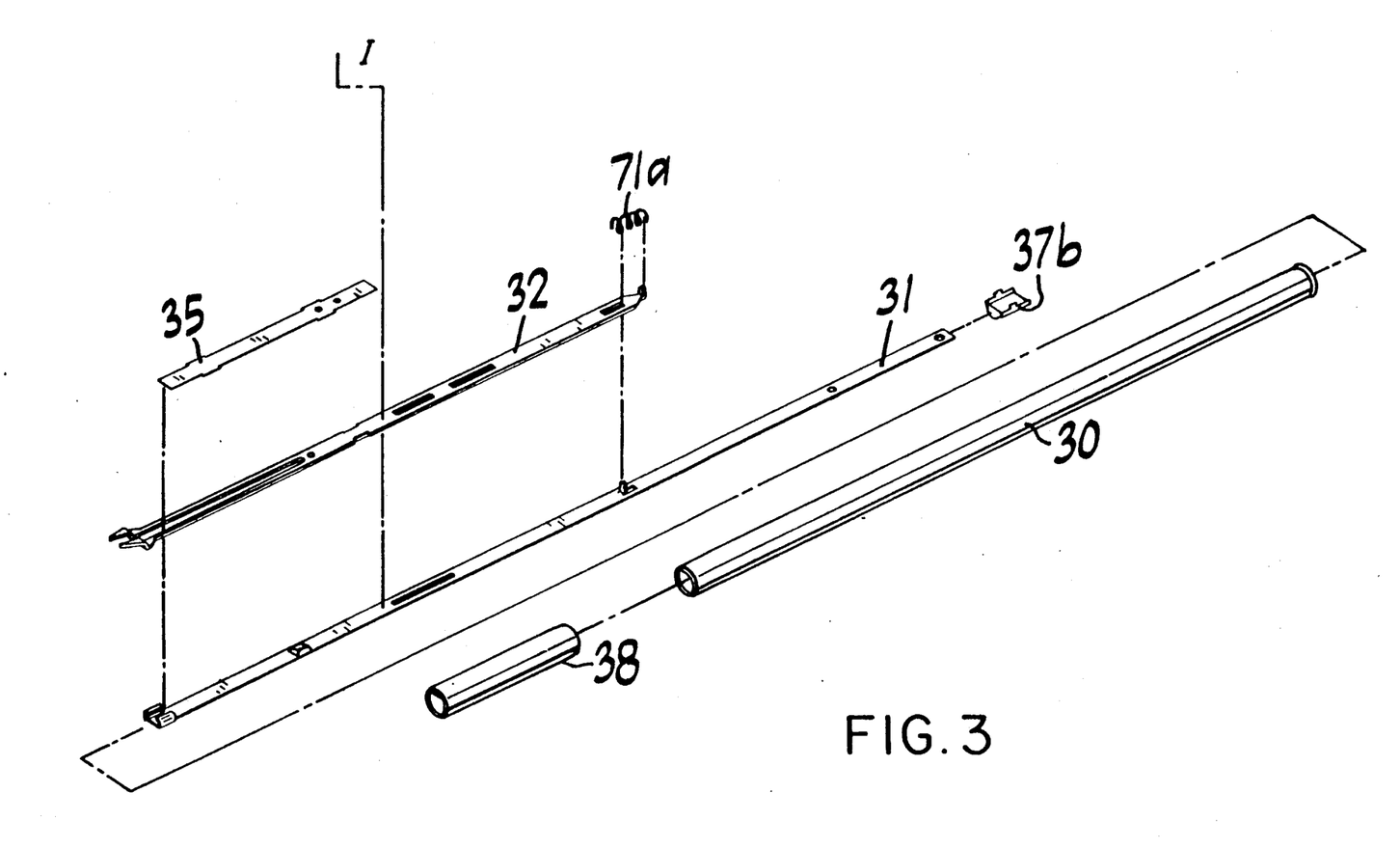
FIG. 3 is an exploded perspective view of the endoscopic hemostatic clip applier of FIG. 1.

The present invention is embodied in an endoscopic hemostatic clip applier designated generally as 10 shown in plan and side elevational views in FIGS. 1 and 2 and in an exploded perspective view in FIG. 3. Applier 10 comprises a housing 12 having bottom and top portions 14 and 16, respectively, and a pair of ring handles 18 and 20 which are pivotally attached to the housing 12. The housing and ring handles are preferably made of a moldable plastic such as polycarbonate but could be metal or any other suitable material. A pair of pivot posts 22 and 23 rise up from the distal end portion of bottom housing portion 14 and each post passes through a hole 24, 25, respectively, at the distal end of ring handles 18, 20. Top housing portion 16 has a pair of pins 26 and 27 which are adapted to be inserted into holes in the corresponding pivot posts 22 and 23, respectively.

Ring handles 18 and 20 are also coupled to housing 12 as well as to other components described below by a pair of link members 28 and 29, respectively. One, distal end of each link member 28, 29 is coupled to the medial portion of its corresponding ring handle by a pivot pin 28a, 29a, respectively, situated distally of the ring portions 18a and 20a of handles 18 and 20. The other, proximal end of each link member 28 and 29 has an aperture by which it is coupled to a pawl yoke member 44 (best seen in FIGS. 8-13), the operation of which will be explained below.

Extending distally from housing 12 within cylindrical tube 30 are the working components of the applier which enable it to operate as intended, these components comprise closure member 31, jaw member 32, drive link 33, clip storage/dispensing cartridge 34 and jaw stabilizer 35. Gasket/spacer inserts 37a and 37b are interposed between the interior of cylindrical tube 30 and the closure member 31 and drive link 33 in order to support these components and provide an additional seal against escape of gases utilized during the endoscopic procedures. Additional gaskets (not shown) may be used in other portions of applier 10 to provide additional seals and a front end tapered tip component 38 may be used to secure the distal tip of the various components and provide a smooth transition to facilitate insertion of applier 10 into a cannula. While the preferred embodiment disclosed herein is shown as an endoscopic clip applier, it will be understood by those skilled in the art that the applier could easily be used for open surgical procedures as well. The working components of applier 10 are joined to yoke 44 by means of the connection between yoke 44 and drive link 33 explained more fully below. Drive link 33 passes from the interior of housing 12 to the exterior through longitudinal track 60 described below and adapter 36. Adapter 36 provides a unique means by which the rectilinear working components of the applier may be easily joined to housing 12. For example, a single housing 12 with its associated moving components may be employed with a differently sized adapter 36 and other working components 30 through 38 in order to produce an endoscopic clip applier suitable for use with differently sized cannulas.

Figure 4:
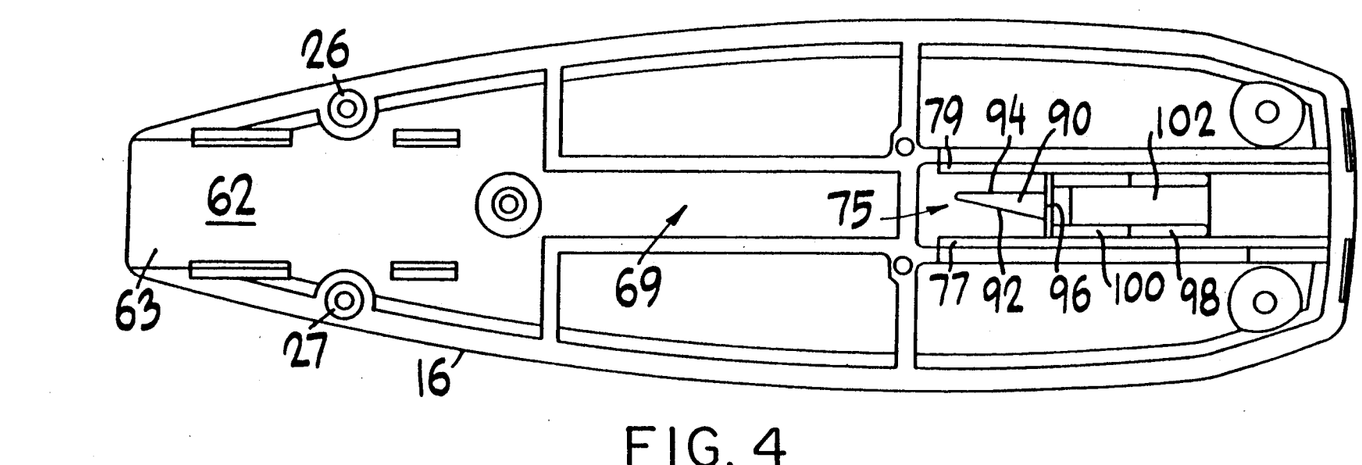
FIG. 4 is a plan view of a portion of the housing of the endoscopic clip applier shown in FIG. 1.
Figure 6:
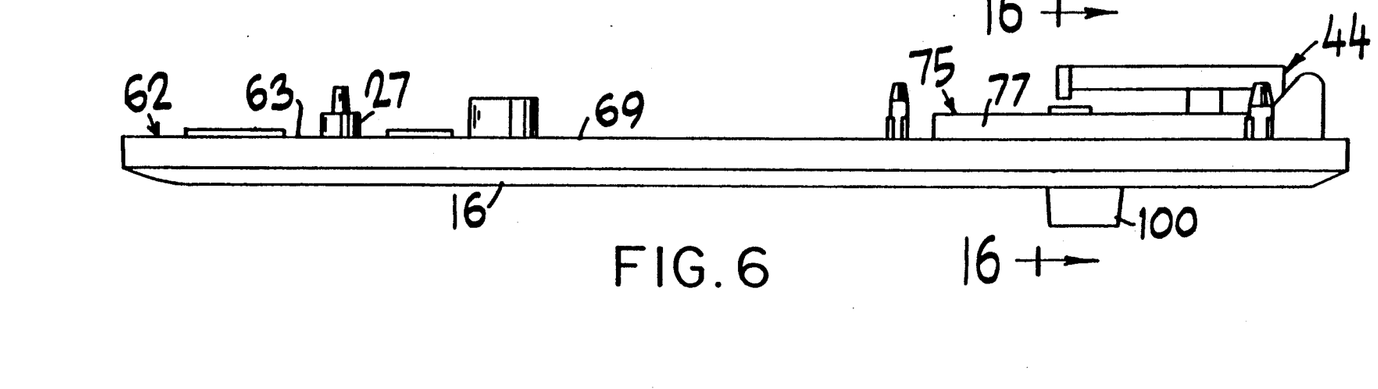
FIG. 6 is a side elevational view of FIG. 5.
Figure 7:
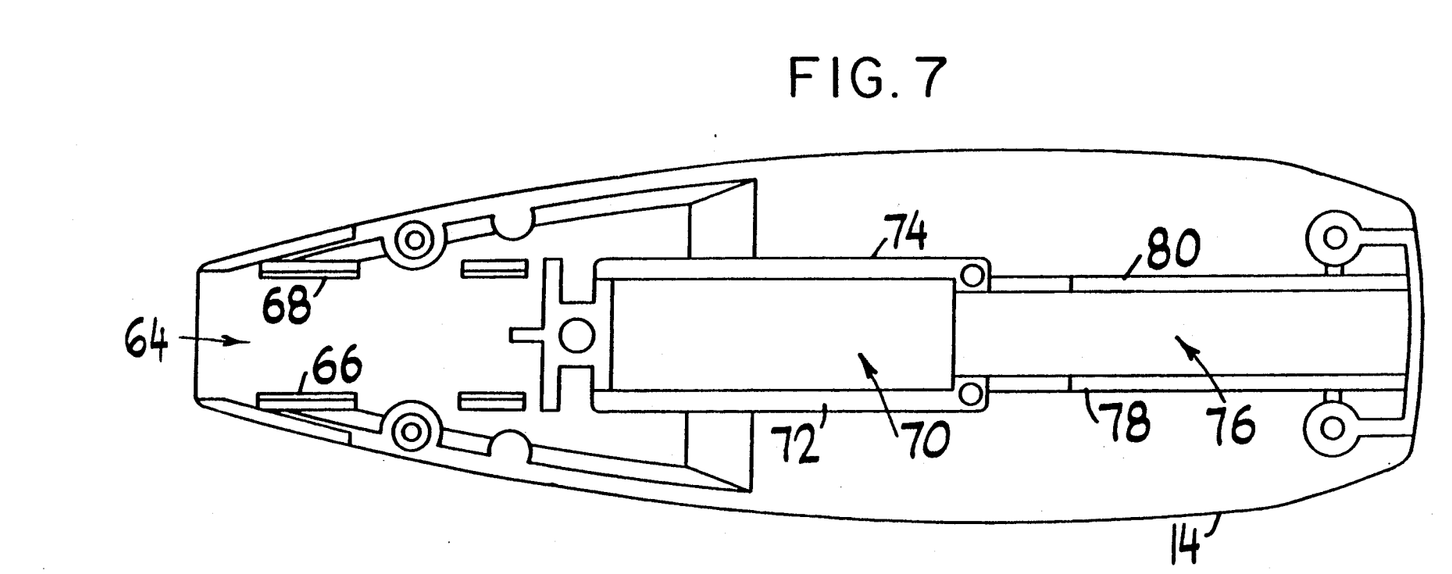
FIG. 7 is a plan view of another portion of the housing of the endoscopic clip applier shown in FIG. 1.
Figure 8:
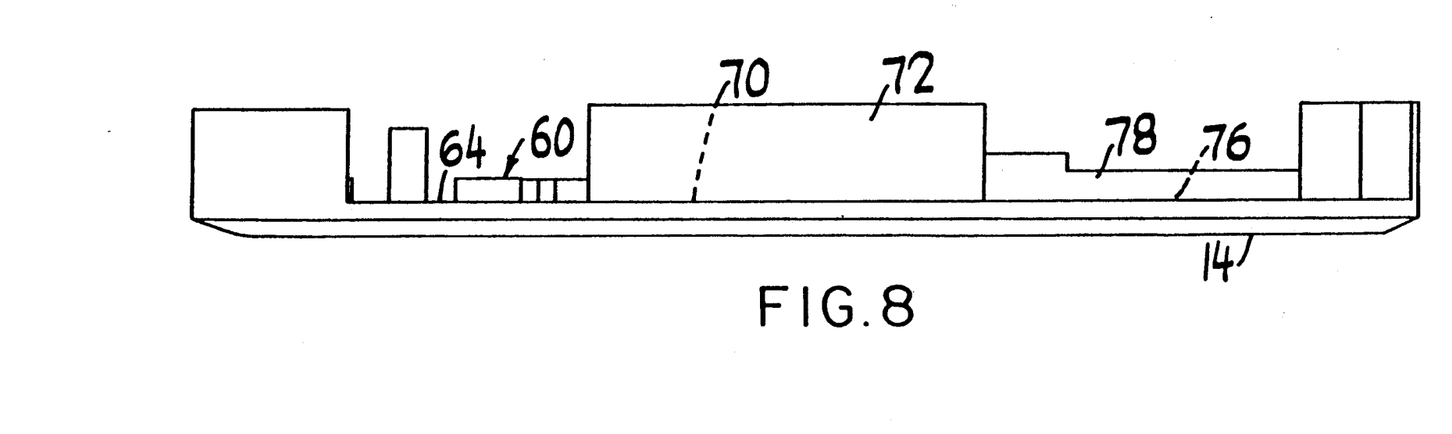
FIG. 8 is a side elevational view of FIG. 7.

Housing 12 has a longitudinal track 60 formed by the cooperative action of top and bottom housing portions 14 and 16 along the longitudinal axis of the applier. Bottom housing portion 14, best seen in FIGS. 7 and 8, has several contiguous, axially aligned track portions including distal-most portion 64, defined in part by spaced apart walls 66 and 68, a center portion 70, defined by parallel walls 72 and 74, and a proximal portion 76, defined by walls 78 and 80. Top housing portion 16, best seen in FIGS. 4, 5 and 6, serves as a longitudinal track cover 62 designed to cooperate with bottom housing portion 14 to form an enclosed longitudinal track 60 for receiving adapter 36 and other components of the applier described below. Track cover 62 comprises distal portion 63 intended to cooperate with distal portion 64, intermediate portion 69 intended to cooperate with center portion 70 and proximal portion 75 intended to cooperate with proximal portion 76. As will be best seen in FIG. 6, track cover portions 63 and 69 do not extend significantly above the plane of the body of housing portion 16 while proximal portion 75 does contain and receive components described below which extend above the plane of housing portion 16 and are intended to cooperate with elements of proximal portion 76 associated with housing portion 14.

Distal track portion 64 is sized to receive adapter 36 and central track portion 70 is sized to receive compression spring 71 which, in conjunction with spring 71a between jaw member 32 and closure member 31 provides biasing forces within applier 10 in a conventional manner.

Proximal track portion 75 comprises a pair of parallel walls 77 and 79 spaced on either side of the longitudinal axis of housing portion 16, and ramp or ratchet member 90 having a surface 92 crossing and laterally inclined relative to the axis of the housing, a surface 94 parallel to and spaced from the axis of the housing and a stop surface 96 transverse to the axis and extending on either side thereof. Situated proximally of surface 96 is an aperture 98 extending through the body of top housing portion 16 into which extends an actuating trigger button 100 situated at the end of a cantilevered arm 102. The internal surface of button 100 is provided with an asymmetrical ramp surface 104 (best seen in FIGS. 16 and 17) the purpose of which will be described below.

Figure 9:
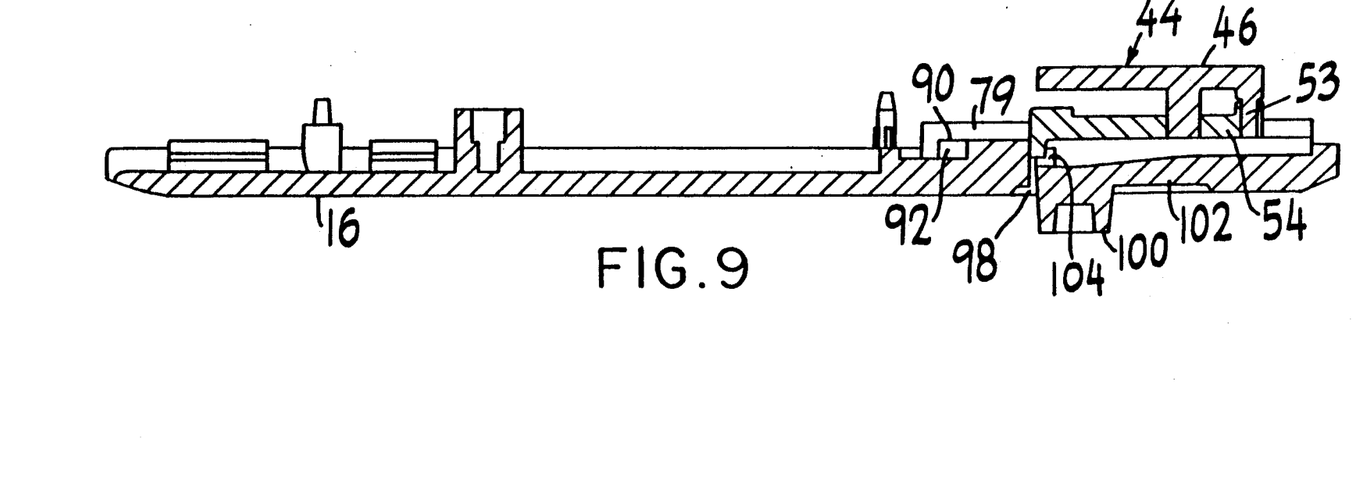
FIG. 9 is a cross-sectional view of FIG. 5 taken along the line 9—9.
Figures 10, 11, 12, 13, 14, 15:
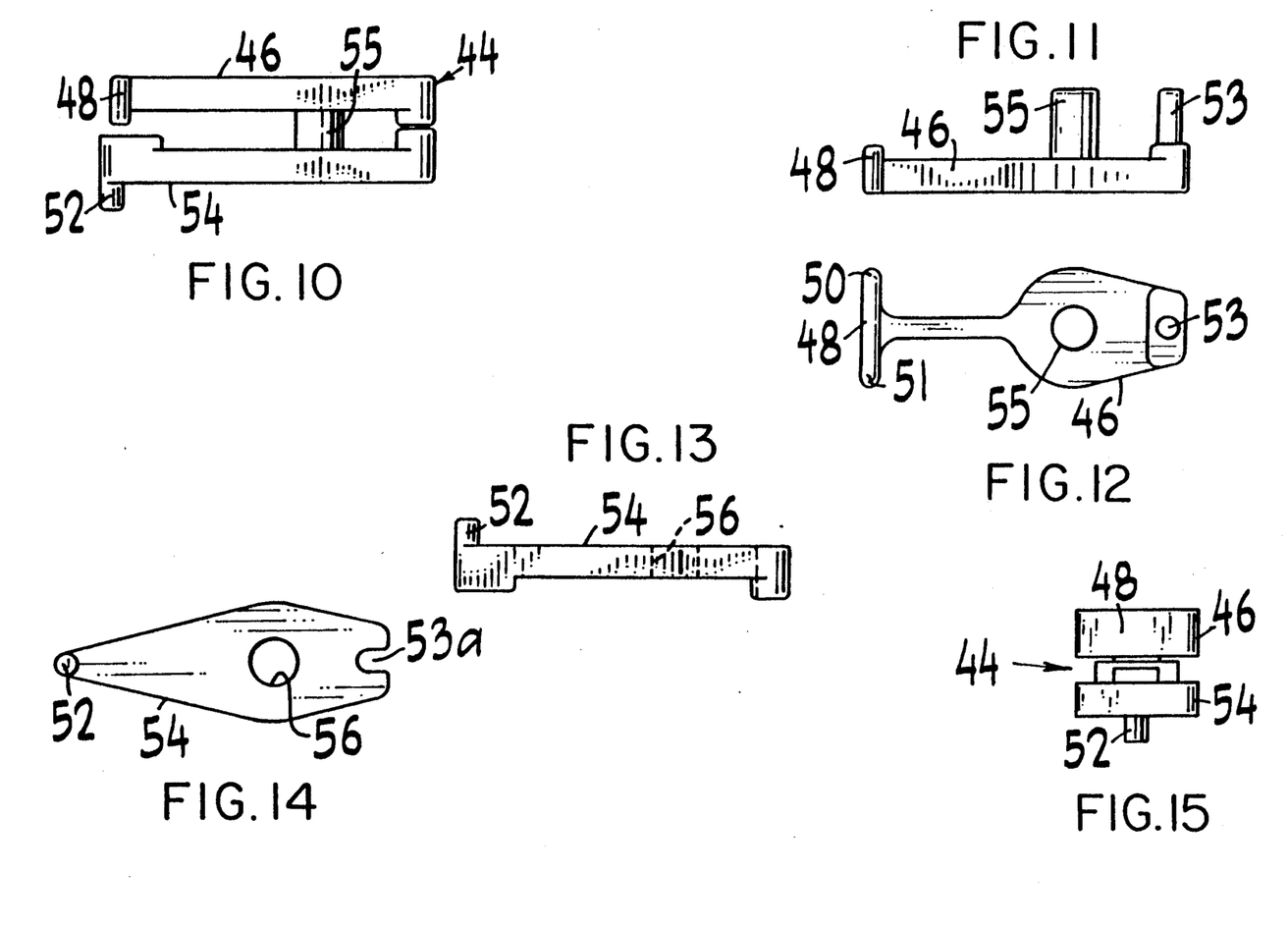
FIG. 10 is a side elevational view of the pawl yoke member used in the endoscopic clip applier and shown in some of the aforementioned drawings.
FIG. 11 is a side elevational view of one portion of the pawl member shown in FIG. 10.
FIG. 12 is a plan view of the pawl member portion shown in FIG. 11.
FIG. 13 is a side elevational view of another portion of the pawl member shown in FIG. 10.
FIG. 14 is a plan view of the pawl member portion shown in FIG. 13.
FIG. 15 is a front elevational view of the pawl member shown in FIG. 10.

As shown in FIGS. 8-13 pawl yoke member 44 comprises a generally U-shaped member having a top leg 46 and a bottom leg 54. As best seen in FIG. 12, top leg 46 has a distal portion provided with a laterally extending bar 48 having ends 50 and 51 which slide between walls 78 and 80 of bottom housing 14, an intermediate body portion provided with a pin 55 extending normally therefrom, and a proximal end provided with a pivot pin 53 parallel to pin 55. Bottom leg 54 has a pawl post 52 located at its distal end, an intermediate body portion provided with an aperture 56 and a proximal end provided with a notch 53a. In the preferred embodiment, top and bottom legs 46 and 54 are separately formed and joined by the cooperative action of pin 55 and aperture 56, and pin 53 and notch 53a. The components of yoke 44 are preferably molded from materials which make yoke 44 resilient and flexible such that top leg 46 can be twisted out of its normal, axial alignment with bottom leg 54 and return into axial alignment with the bottom leg when the twisting force is removed.

As best seen in FIG. 3, the proximal ends of drive link 33 and link members 38a and 38b are pivotally connected to pawl yoke 44 between its top and bottom legs by pin 55 passing through aligned holes in the proximal ends of the drive link and link members.

Figure 5:
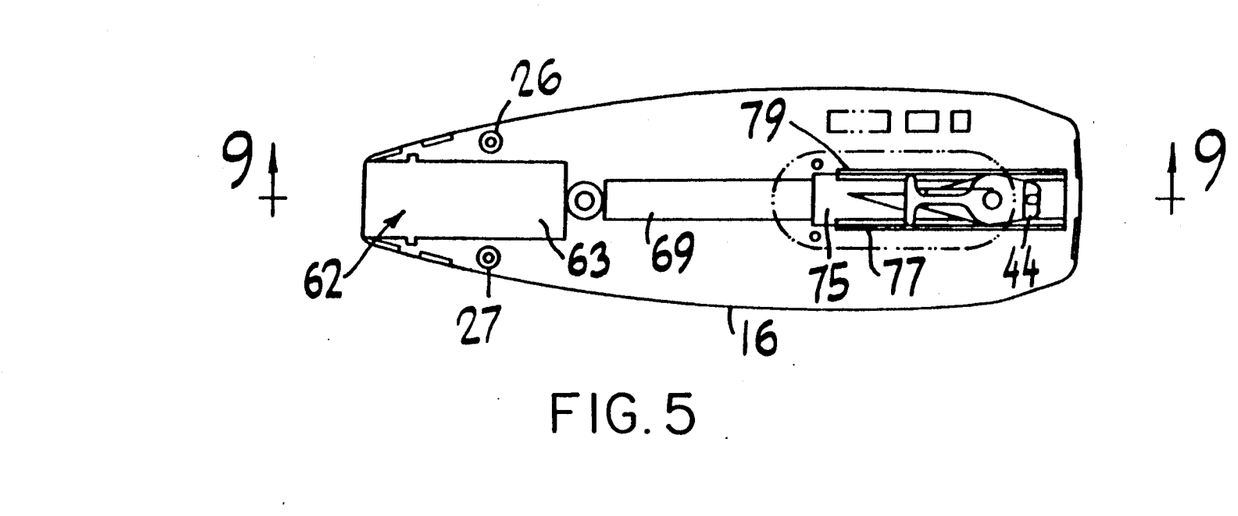
FIG. 5 is a plan view of the housing portion shown in FIG. 4 with a pawl yoke member in place.
Figure 16:
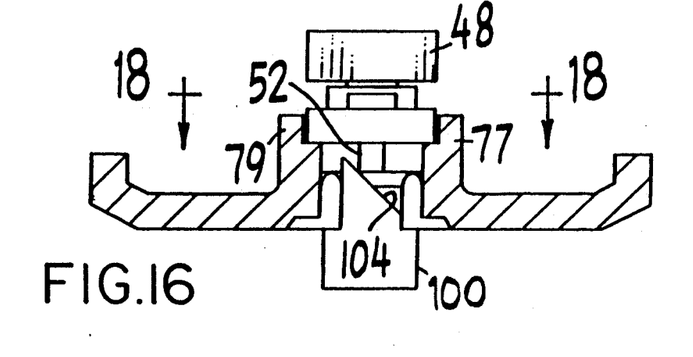
FIG. 16 is a cross sectional view of FIG. 6 taken along the line 16—16.
Figure 17:
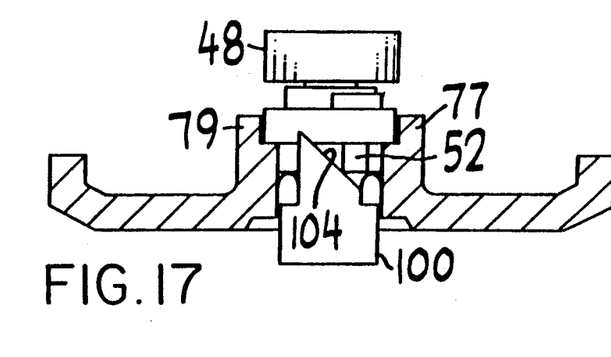
FIG. 17 is a view of FIG. 16 showing the placement of the components in a particular part of their cycle of operation.
Figure 18:
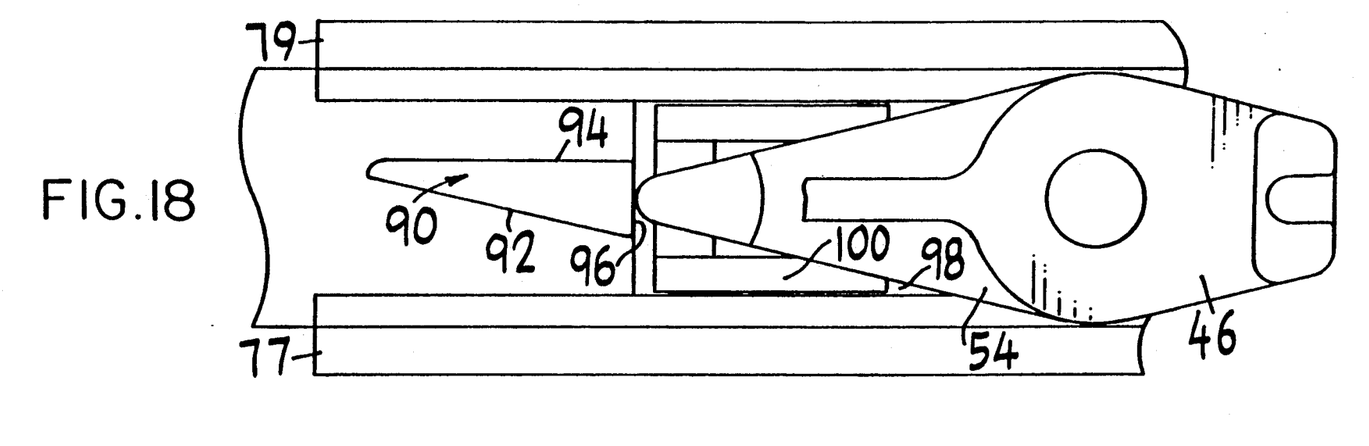
FIG. 18 is a view of FIG. 16 taken along the line 18—18.

The operation of the invention may best be understood by reference to FIGS. 5 and 15-18. It will be understood that the operation of applier 10 is cyclical and, for ease of explanation the beginning of the cycle will be chosen as the point where the handles 18, 20 are in their extreme open position. At this point pawl yoke 44 will be at its distal-most position within track 60 with crossbar 48 being distal of ramp member 90. Because of the connection between handles 18 and 20 and pawl yoke 44, as the handles are squeezed together the pawl yoke will move proximally from a position where crossbar 48 is distal of ramp 90 to a position proximal of ramp 90 as shown in FIGS. 5 and 9. In a manner analogous to the operation of the clip applier described in the aforementioned copending application, as yoke member 44 moves distally, post 52 will ride up surface 92 until it clears the rear of ramp member 90 at which point, because of the inherent resilience of yoke member 44, post 52 will return to its normal alignment with the axis of the applier and position itself on the centerline in contiguous, abutting engagement with surface 96. This position is best shown in FIGS. 16 and 18. At this point in the cycle of operation of the applier the spring 71 is compressed (by tabs 91 and 93 on drive link 33) and yoke 44 is urged against surface 96. It will be understood that stop surface 96 prevents distal motion of yoke member 44 and all components connected to it including the drive link and feeding components connected to it (not shown). When a user desires to feed a clip he must do so by actuating the drive link by depressing button 100 to a position as shown in FIG. 17 at which the internal ramp surface 104 of button 100 urges post 52 laterally, twisting yoke member 44 to a point where post 52 will clear the edge of stop surface 96. Spring 71 will then cause drive link 33 to move distally to feed a clip as described in the aforementioned copending application. Continual squeezing of the ring handles closes the jaws as in the prior embodiment.

While the preferred embodiment utilizes a combination of elements that require post 52 to be pushed laterally in order to disengage it from stop surface 96, other designs would be equally workable. For example, a ramp surface (analogous to surface) 92 could be transversely inclined and the post could be pressed transversely to clear a stop surface and perform a similar function to that of the preferred embodiment.

During the first portion of the cycle of operation of applier 10, as handles 18 and 20 are squeezed together the jaws of the applier are urged together whether or not a clip is in position between the jaws. Closure of the jaws occurs essentially because of the proximal motion of the jaw member 32. While the normal operation of a clip applier intended for open surgery (such as that described in the aforementioned copending patent application) may be to have the drive link move proximally along with the jaw members as the handles are being squeezed together and subsequently have the drive link feed a clip between the jaws as the handles are open, in the present invention the opening of the handles and, consequently, the forward movement of the drive link and the associated feeding of the clip is prevented by the abutting engagement between pin 52 and stop surface 96.

While in the prior embodiment (disclosed in the aforementioned copending application) the activating and sequencing means activated the feeder to move a clip into the jaws as the lever means was returned from the closed position to the open position, the subject invention does not have such automatic feeding. As the lever means is moved from the open position to the closed position, the pawl member 44 engages a stop surface 96 which prevents the lever means from activating the feeder as tension on the lever handles is relaxed. While in the prior embodiment means were provided for prevented feeding of another clip into the jaws until after the lever handles were moved into the closed position (the means comprising a detent in the cam track in the body housing and a cam track follower coupled to the lever means) it is desirable in endoscopic applications to have the surgeon control the feeding of the clip rather than having this feeding be automatic. Consequently, the present invention is intended to produce an instrument which requires the operator to actively trigger something to release this mechanism.

It will be understood by those skilled in the art that numerous modifications and improvements may be made to the preferred embodiment of the invention described herein without departing from the spirit and scope thereof.

What is claimed is:

1. In an instrument for applying surgical ligating clips, said instrument comprising a housing, a first activating mechanism for feeding the clips successively to a position in which they may be crimped and a second activating mechanism for crimping a clip at said position, the improvement comprising:
   trigger means for selectively enabling the operation of said first activating mechanism, said trigger means comprising:
   pawl means operatively secured to said first activating mechanism and adapted to slide within said housing along a predetermined track;
   a pawl post attached to said pawl means and deflectable from a normal, unbiased position to a biased position as said pawl means slides proximally;
   ramp means fixedly situated relative to said predetermined track and adapted to have said pawl post slidably move along said ramp means as said pawl means slides proximally;
   stop means to engage said pawl post to prevent it from moving distally beyond a predetermined point along said track;
   means operable by a user of said instrument to disengage said pawl post from said stop means.

2. An instrument according to claim 1 wherein said pawl means is in its normal, unbiased position when it is in engagement with said stop means and wherein said disengagement means comprises means to deflect said pawl means to a predetermined, biased position at which it will be clear of said stop means and free to move distally thereof.

3. An instrument according to claim 1 wherein said stop means is a wall situated astride the axis of said predetermined track, normal thereto, and wherein said pawl means during part of its cycle of operation is urged distally against said stop means by a spring operatively associated with said first activating mechanism.

4. An instrument according to claim 1 wherein said disengagement means comprises a trigger accessible from the exterior of said housing, said trigger comprising a cantilevered arm integrally formed with said housing and a cam surface situated at the free end of said arm and facing into the interior of said housing and adapted to engage said pawl post when it is engaged with said stop means, whereupon motion of said cam surface into the interior of said housing will cause disengagement of said pawl post from said stop means.

5. An instrument according to claim 4 wherein said pawl post is laterally deflectable and said disengagement means is adapted to laterally deflect same to disengage it from said stop means.

6. An instrument according to claim 4 wherein said pawl post is transversely deflectable an said disengagement means is adapted to transversely deflect same to disengage it from said stop means.

* * * * *